United States Patent [19]

Polito et al.

[11] 4,081,244

[45] Mar. 28, 1978

[54] IMMUNOASSAY PROCEDURE EMPLOYING NOVEL IMMUNOCHEMICAL COMPOSITES

[75] Inventors: Alan J. Polito, Costa Mesa; William S. Knight, Laguna Beach, both of Calif.

[73] Assignee: Beckman Instruments, Inc., Fullerton, Calif.

[21] Appl. No.: 682,807

[22] Filed: May 3, 1976

[51] Int. Cl.² .................. G01N 31/06; G01N 33/16
[52] U.S. Cl. .................. 23/230.6; 23/230 B; 195/63; 195/DIG. 11; 424/1; 424/1.5; 424/12; 260/112 B
[58] Field of Search ............... 23/230 B, 230.6; 424/1, 424/1.5, 12; 195/63, DIG. 11; 260/112 B

[56] References Cited

U.S. PATENT DOCUMENTS

| 3,555,143 | 1/1971 | Axen | 424/1 |
| 3,645,852 | 2/1972 | Axen | 424/1 X |
| 3,867,366 | 2/1975 | Rubenstein | 424/1 X |
| 3,896,217 | 7/1975 | Johnson | 424/1 |
| 3,904,478 | 9/1975 | Dean | 195/DIG. 11 |
| 3,914,183 | 10/1975 | Johansson | 195/DIG. 11 |
| 3,947,352 | 3/1976 | Cuatrecasas | 195/DIG. 11 |
| 3,975,511 | 8/1976 | Vann | 424/1.5 |
| 3,980,765 | 9/1976 | Broussalian | 424/1 |
| 4,002,532 | 1/1977 | Weltman | 195/63 X |

OTHER PUBLICATIONS

Ratcliffe, *Br. Med. Bull.*, 30:32 (1974).
Seki et al., *Endocrinol. Japan*, 20:121 (1973).
Koninckx et al., *Acta Endocrinol.*, 81:43 (1976).
Wide et al., *Biochem. Biphys. Acta*, 130:257 (1966).
Axen et al., *Nature* (Lond.), 214:1302 (1967).
Wide, *Acta Endocrinol*, (Copenhagen) Suppl. No. 142:207 (1969).
Bolton et al., *Biochemica et Biophysica Acta*, 329:318 (1973).
Zeltner et al., *Clin. Chem.*, 20:5 (1974).
Der Hollander et al., *J. Immunol. Methods*, 1:247 (1972).
Chan et al., *Ann. Clin. Biochem.*, 12:173 (1975).
Immobilized Enzymes, Antigens, Antibodies and Peptides, edited by Howard H. Weetall, Marcell Decker, Inc., New York, N.Y. (1975), Chapter 4.
Immobilized Enzymes, Antigens, Antibodies and Peptides, edited by Howard H. Weetall, Marcell Decker, Inc., New York, N.Y. (1975), Chapter 9.

*Primary Examiner*—Sidney Marantz
*Attorney, Agent, or Firm*—Robert J. Steinmeyer; Robert S. Frieman

[57] ABSTRACT

A method of separating free from bound fractions in an immunoassay procedure of the type wherein a solution is contacted with a composite comprising a finely divided, activated, polysaccharide matrix covalently coupled to a primary antibody, wherein the improvements comprise:

(a) coupling an α,ω-diaminospacer to said finely divided, activated, polysaccharide matrix via one of said α,ω-diaminospacers's amino groups thereby forming a finely divided, derivatized, polysaccharide matrix;

(b) covalently coupling said finely divided, derivatized, polysaccharide matrix to an antibody selected from a group consisting of primary and secondary antibodies via a bifunctional coupling agent having a formula

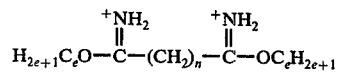

wherein n is an integer from 1 and 6 and wherein e is an integer from 1 to 2; and (c) using a polysaccharide matrix having an average wet maximum dimension of 1 to 18 μ.

13 Claims, No Drawings

4,081,244

IMMUNOASSAY PROCEDURE EMPLOYING NOVEL IMMUNOCHEMICAL COMPOSITES

BACKGROUND OF THE INVENTION

1. Field of the Invention

This invention pertains to a method of separating free from bound fractions in an immunoassay procedure and to a novel immunochemical composite for use therein.

2. Description of the Prior Art

The end-point of any competitive binding analysis involves determining the relative proportion of antigen (or hapten) that is free and antigen (or hapten) that is bound to the saturable binder. Current basic separation techniques involve differential migration of bound and free fractions (i.e., paper chromatoelectrophoresis, gel filtration), adsorption methods (i.e., charcoal, silicates), fractional precipitation (i.e., ammonium sulfate, polyethylene glycol), and a double antibody method. According to J. G. Ratcliffe, Br. Med. Bull., 30:32 (1974), an ideal separation technique should fulfill the following criteria:

A. It must completely separate bound and free fractions with a wide margin for error in the conditions used for separation.

B. It must be simple, quick, cheap, and use reagents and equipment that are readily available.

C. It should be unaffected by plasma or serum. Ratcliffe further notes that for general clinical application, all manipulations should be performed in a single tube, be suitable for automation, and be applicable to a wide range of antigens or haptens (i.e., small peptides and steroids as well as large molecular weight proteins).

Although the double antibody method for separation of free and bound fractions in radioimmunoassay (RIA) systems in currently one of the most widely employed separation techniques and under optimum conditions satisfies most of the criteria mentioned above, it does possess certain inherent disadvantages. See J. G. Ratcliffe, supra; K. Seki and M. Seki, Endocrinol. Japan, 20:121 (1973); and P. Koninckx, R. Bouillon, and P. De Moor, Acta Endocrinol., 81:43 (1976). Since carrier protein must be added, large quantities of selected precipitating antibody are required and thus the method is expensive. It requires considerable length of time for the immunoprecipitation reaction to reach equilibrium (24 to 48 hours at 4° C.). Finally, due to the possibility of aspecific interferences by factors present in the serum, the conditions of the assay must be meticulously evaluated before establishing an assay system.

Antibodies coupled to cyanogen bromide-activated dextran and cellulose particles are widely used in RIA systems as a result of the work of Wide, Porath, and Axen (L. Wide and J. Porath, Biochem. Biophys. Acta, 130:257 (1966)), R. Axen, J. Porath and S. Ernback, Nature (Lond.), 214:1302 (1967), and L. Wide, Acta Endocrinol. (Copenhagen) Suppl. No. 142:207 (1969)). A. E. Bolton and W. H. Hunter, Biochemica et Biophysica Acta, 329:318 (1973), reported that recovery of primary antibody activity tended to be higher on cyanogen bromde activated solid preparations of antisera to haptens and small peptides than to similar solid phase preparations of antisera to large molecular weight protein hormones. Thus one of the main disadvantages in the use of solid phase primary antibodies in RIA systems is that as a result of the loss of antibody titer and avidity which often occurs during the coupling step, one must develop longer, more expensive and more complicated systems (i.e., sequential assays). (A. Zeltner and P. E. Duly, Clin. Chem., 20:5 (1974)). Recently, F. C. Den Hollander, A. H. W. M. Shurrs, and H. Zan Hell, J. Immunol. Methods, 1:247 (1972), developed a new separation method employing second antiserum coupled to an insoluble matrix by use of cyanogen bromide and called the separation method and double antibody solid phase (DASP) method. Although the titer and avidity of the second antibody is most certainly reduced in these solid preparations, the primary antibody reaction remains unaltered and thus one of the main disadvantages of solid phase systems is circumvented. In fact, the DASP method possesses the following advantages over the more conventional soluble double antibody method of separation of free and bound fractions:

A. Since solid preparations of precipitating antibody require little or no carrier protein, less second antibody is required to precipitate the first antibody.

B. The DASP method requires less time for complete separation of free and bound fractions.

C. Aspecific interferences by factors present in the serum are totally absent with the DASP precipitation if one works in the area of excess second antibody. In fact, once optimal conditions for precipitation of the immune complex are established, no frequency reassessment is required.

For all the pluses one obtains with solid preparations of precipitating antibody, there remains one mechanical disadvantage common to all solid phase assays. It is necessary in all solid phase assays to agitate the reactants continuously with the additional extra task of first stoppering the assay and then centrifuging and unstoppering them prior to the washing step. V. Chan, C. Merrett, J. Landon, A. M. Linden, and M. Joustra, Ann. Clin. Biochem., 12:173 (1975), coupled primary antibodies to cyanogen bromide activated Sephadex G25 brand, ultrafine, bead-formed, dextran gel (less than 10 $\mu$ particle size) and reported that will small incubation volumes (300 to 400 microliters) it is possible for the antibody reaction to proceed without the need for vertical rotation or any other means of continuous agitation.

It has been discovered that immunochemical composites containing a finely divided derivatized polysaccharide matrix wherein the polysaccharide matrix has an average wet maximum dimension of 1 to 18 $\mu$ and also containing positively charged imidoesters which covalently couple said finely divided, derivatized, polysaccharide matrix to an antibody are excellent means for separating free from bound fractions without the need for vertical rotation or any other type of continued agitation. Further, the novel immunochemical composites within the scope of this invention display an amount of activity which far exceeds the activity displayed by the immunochemical composites prepared by Chan et al.

SUMMARY OF THE INVENTION

This invention encompasses a method of separating free from bound fractions in an immunoassay procedure of the type wherein a solution is contacted with a composite comprising a finely divided, activated, polysaccharide matrix covalently coupled to a primary antibody, wherein the improvements comprise:

(a) coupling an α,ω-diaminospacer to said finely divided, activated, polysaccharide matrix via one of said α,ω-diaminospacer's amino groups thereby forming a finely divided, derivatized, polysaccharide matrix;

(b) covalently coupling said finely divided, derivatized, polysaccharide matrix to an antibody selected from a group consisting of primary and secondary antibodies via a bifunctional coupling agent having a formula

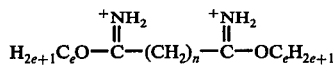

wherein $n$ is an integer from 1 to 6 and wherein $e$ is an integer from 1 to 2; and (c) using a polysaccharide matrix having an average wet maximum dimension of 1 to 18 $\mu$.

Also within the scope of this invention is an immunochemical composite for separating free from bound fractions in an immunoassay procedure of the type having a finely divided, activated, polysaccharide matrix covalently coupled to a primary antibody, wherein the improvements comprise:

(a) coupling an $\alpha,\omega$-diaminospacer to said finely divided, activated, polysaccharied matrix via one of said $\alpha,\omega$-diaminospacer's amino groups thereby forming a finely divided, derivatized, polysaccharide matrix;

(b) covalently coupling said finely divided, derivatized, polysaccharide matrix to an antibody selected from a group consisting of primary and secondary antibodies via a bifunctional coupling agent having a formula

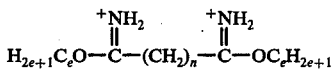

wherein $n$ is an integer from 1 and 6 and wherein $e$ is an integer from 1 to 2; and (c) using a polysaccharide matrix having an average wet maximum dimension of 1 to 18 $\mu$.

DESCRIPTION OF THE PREFERRED EMBODIMENTS

The immunoassay procedure of this invention entails contacting a solution containing free and bound fractions with a novel immunochemical composite via techniques well known to those skilled in the art of immunoassay and thereby separating the free from the bound fractions. See D. M. Weir, "Immunology for Undergraduates", Churchill Livingstone, Edinburgh, England (1973) and J. G. Ratcliffe, *British Medical Bulletin*, 30:32 (1974), said publications being incorporated herein in toto by reference. Preferably, the immunoassay procedure entails a method in which continuous agitation and thereby the need to stopper the tubes is eliminated. See V. Chan, C. Merrett, J. Landon, A. M. Linden, and M. Joustra, *Ann. Clin. Biochem.*, 12:173 (1975), said publication being incorporated herein in toto by reference. More preferably, the immunoassay procedure is an RIA procedure which techniques are also well known to those skilled in the art. See C. S. Skelley, L. P. Brown, and P. K. Besch, "Radioimmunoassay", *Clinical Chemistry*, Vol. 19, No. 2, 146 to 186 (1973), said publication being incorporated herein in toto by reference.

Another method within the scope of this invention entails the above described procedures except that the composite used therein is not the novel immunochemical composite mentioned above and described in more detail below but an immunoassay reagent comprising a finely divided, polysaccharide matrix covalently coupled to a secondary antibody via any of the various techniques known to those skilled in the art. Although this latter method does not have the degree of efficacy found in the other above described methods of this invention (see examples and discussion below), nevertheless, it is a marked improvement and possesses distinct advantages over the prior art primary antibody methods such as that of Chan et al.

In prior art suspension methods, the primary antibody is attached to a matrix, thereby adversely interfering with the primary antibody-large antigen biological reaction. Also, these prior art methods require an accurate addition of gel (i.e., composites comprising primary antibodies bound to matrices) which creates a constant source of error. However, suspension methods within the scope of this invention which use secondary antibodies attached to matrices eliminate both of the above described prior art problems.

The novel immunochemical composite within the scope of this invention comprises a finely divided, derivatized, polysaccharide matrix covalently coupled to an antibody by a bifunctional coupling agent. The polysaccharide matrix can be any matrix having a plurality of hydroxyl groups attached thereto, as well as derivatives thereof. Preferred polysaccharide matrices include cellulosic polymers, dextran polymers, agarose, and derivatives thereof. Cellulosic polymers and derivatives thereof are the polysaccharide matrices of choice.

The first essential requirement of this invention is that the polysaccharide matrix must be finely divided and have an average wet maximum dimension of 1 to 18 $\mu$, preferably 10 to 15 $\mu$. The polysaccharide matrix may be spherical, linear, or have any other geometric configuration, provided that its average wet maximum dimension (diameter, side, length) is as described above. Several types of polysaccharide matrices are commercially available in this finely divided form, for example, Sephadex brand, bead-formed, dextran gel is available in several grades having a dry particle diameter of 10 to 40 $\mu$ as well as less than 10 $\mu$. It is also possible to reduce the polysaccharide matrices average wet maximum dimension by chemical techniques, for example by hydrolysis.

The finely divided, polysaccharide matrices can be activated by any suitable method known to those skilled in the art. Exemplary reagents suitable for activating the polysaccharide matrix include cyanogen halide, epihalohydrin, haloacetyl halides, and divinylsulphone. See F. A. Patty, *Industrial Hygiene and Toxicology*, Vol. 2, p. 634, Interscience, New York, N.Y. (1949), R. Axen, J. Porath, and S. Ernback, *Nature* (Lond.), 214:1302 (1967), W. Rosner and R. N. Smith, *Biochem.*, 14:4813 (1975), A. Jagendorph, A. Patchornik, and M. Sela, *Biochimica et Biophysica Acta*, 78:516 (1963), and J. Porath and L. Sundberg, *Nature New Biol.*, 238:261 (1972), said publications being incorporated herein in toto by reference. Preferably, a cyanogen halide or an epihalohydrin reagent is used to activate the finely divided, polysaccharide matrix. More preferably, the finely divided, polysaccharide matrix is activated by an epihalohydrin reagent or mixture thereof and most preferably, the finely divided, polysaccharide matrix is activated by epichlorohydrin.

The second essential requirement of this invention is the use of a finely divided, derivatized, polysaccharide matrix which is formed by coupling an $\alpha,\omega$-diaminospacer to the above activated, finely divided, polysaccharide matrix via one of the α,ω-diaminospacer's amino groups. To illustrate an exemplary finely divided, derivatized, polysaccharide matrix, if the finely divided polysaccharide matrix has been activated by a cyanogen halide reagent, the derivatized, finely divided, polysaccharide matrix will have the formula

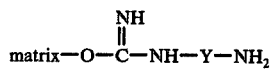

wherein matrix is a finely divided, polysaccharide matrix as defined above and wherein Y is a spacer. Exemplary spacers include $-(CH_2)_m-$, $-(CH_2)_b-NH-(CH_2)_c-$,

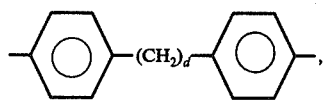

and

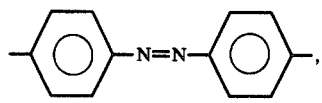

wherein $m$ is an integer from 1 to 12, preferably from 4 to 6, wherein $b$ and $c$ independently are integers from 1 to 6, preferably 2 to 3, and wherein $d$ is an integer from 1 to 10, preferably 2 to 4. Preferably, Y is $-(CH_2)_m-$.

As a further illustration of an exemplary finely divided, derivatized polysaccharide matrix, if the finely divided polysaccharide matrix has been activated by an ephihalohydrin reagent, the derivatized, finely divided polysaccharide matrix will have the formula

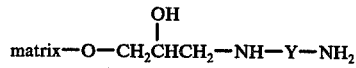

wherein matrix and Y are as defined above.

The antibody to which the derivatized, finely divided polysaccharide matrix is covalently coupled can be either a primary antibody or a secondary antibody. Since this invention's sole requirement is that the antibody possess a lysine residue, virtually all primary and secondary antibodies can be covalently coupled to the derivatized polysaccharide matrix because all antibodies possess such lysine residues. Preferably, the antibody is a secondary antibody.

The third essential requirement and crux of this invention is the use of imidoesters as the coupling agent for the novel immunochemical composite. The imidoester has the general formula

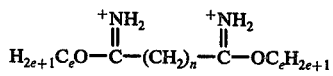

wherein $n$ is an integer from 1 to 6, preferably from 4 to 6, and wherein $e$ is an integer from 1 to 2. The use of these imidoesters enables one to covalently attach antibodies to solid supports through known chemical reactions which immobilize both primary and secondary antibodies through their lysine residues which in most instances are not essential for immunological activity. Further, the presence of a positively charged matrix does not cause adverse nonspecific adsorption onto this invention's novel immunochemical composite.

The novel immunochemical composites within the scope of this invention can be prepared in accordance with the following general procedure. A finely divided polysaccharide matrix is either commercially obtained or prepared by hydrolyzing a polysaccharide matrix. In order to hydrolyze said matrix, the polysaccharide matrix is contacted with an acidic solution, e.g., a 3 to 10 N solution of hydrochloric, sulfuric, or other suitable acid for a sufficient period of time, e.g., 2 to 24 hours. The acidic mixture is then neutralized with a basic solution, e.g., a 3 to 10 N solution of sodium or potassium hydroxide, etc., and subsequently washed and dried via standard techniques.

An activating reagent is then contacted with the finely divided polysaccharide matrix in a solution having a desirable pH. The pH can be in a general range from about 7.5 to about 10.0 with the particular pH being dictated by the activating reagent and finely divided polysaccharide matrix being used. The reaction can be allowed to proceed at room temperature. The activating reagent is allowed to remain in contact with the finely divided polysaccharide matrix for a sufficient period of time, from about 5 minutes to 5 hours, to enable the matrix to become activated. The excess activating reagent is removed from the activated, finely divided polysaccharide matrix by washing said matrix with a suitable medium, e.g., water, buffer (e.g., sodium bicarbonate), etc. The activated matrix is then suspended in a suitable medium, e.g., an aqueous solution of dimethylformamide. The desired α,ω-diaminospacer is then added to the suspended, activated, finely divided, polysaccharide matrix and the reaction is allowed to proceed for about 1 to 10 hours at room temperature. The excess α,ω-diaminospacer is removed from the derivatized, finely divided, polysaccharide matrix by washing said matrix with a suitable medium, e.g., a solution of dimethylformamide, followed by a washing with a suitable buffer, e.g., sodium bicarbonate buffer. After this double washing procedure, the derivatized, finely divided, polysaccharide matrix is suspended in a suitable buffer, e.g., a sodium bicarbonate buffer.

The bifunctional coupling agent or mixture thereof is dissolved in a basic solution at about 4° C. If necessary, the pH is adjusted to about 8 to 9. The suspended, derivatized, finely divided, polysaccharide matrix is then contacted with the dissolved bifunctional coupling agent and the mixture is rotated at about 4° C. for 1 to 5 hours.

After removing the excess bifunctional coupling agent, the coupled, derivatized, finely divided, polysaccharide matrix is suspended in a mixture containing a suitable buffer, e.g., a sodium bicarbonate buffer, and a primary or secondary antibody function. The mixture is rotated for about 10 to about 24 hours in a cold environment. The immunochemical composite is then thoroughly washed with a suitable buffer, e.g., a sodium bicarbonate buffer, and then suspended in a suitable buffer having a pH of about 8, e.g., a barbital buffer containing about 0.1% gelatin.

The novel immunochemical composite within the scope of this invention and as prepared by the above general procedure has the schematic structure finely divided, derivatized, polysaccharide

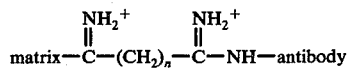

wherein finely divided, derivatized, polysaccharide matrix, n, and antibody are as defined above. The preferred immunochemical composite within the scope of this invention has a formula

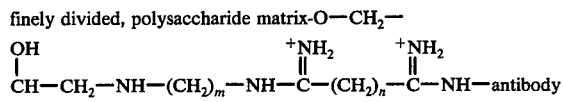

wherein finely divided, polysaccharide matrix, m, n, and antibody are as defined above.

The following examples are provided for the purpose of further illustration only and are not intended to be limitations on the disclosed invention.

EXAMPLE 1

Microcrystalline cellulose (9 gm) type 50 (50 μ average particle size) was added to 30 ml of a 6N hydrochloric acid solution and the mixture was stirred for a period of 4 hours at room temperature. After the 4 hour reaction time, the mixture was neutralized with a 6N solution of sodium hydroxide and the hydrolized cellulose was washed with 1,200 ml of water. The packed cellulose was further washed with 300 ml of methanol followed by 100 ml of diethyl ether. The gel residue was suspended in 100 ml of ether and dried under reduced pressure.

Example 1 was repeated several times with the sole modification being the reaction time. The reaction time was varied from 4 hours to periods of 6, 24, and 64 hours. A microscopic examination disclosed that the microcrystalline cellulose Type 50 which had been hydrolyzed for 4 to 6 hours had an average wet length of approximately 15 to 20 μ and those which had been hydrolyzed for 24 and 64 hours had an average wet length of approximately 10 to 12 μ.

EXAMPLE 2

Epichlorohydrin (3 ml) was added to a mixture of 6 gms of microcrystalline cellulose Type 50 in 30 ml of 1N sodium hydroxide with vigorous stirring at room temperature. After 2 hours, the excess epichlorohydrin was removed by washing with 1 liter of water. The washed, activated, cellulosic matrix was then suspended in 60 ml of a 50% aqueous solution of dimethylformamide. To this suspended, activated matrix was added 0.85 gms of 1,6-hexanediamine. The reaction was allowed to proceed with stirring for 2 hours at room temperature and then the excess 1,6-hexanediamine was removed by washing with 1 liter of a 50% aqueous solution of dimethylformamide. After washing with 1 liter of 0.1M sodium bicarbonate, the derivatized, cellulosic matrix was suspended in 0.1M sodium bicarbonate to give a 1:1 mixture of derivatized matrix to sodium bicarbonate.

Dimethylsuberimidate (DMS; 0.80 gm; 3 m moles) was dissolved in 0.6 ml of cold 5N sodium hydroxide solution with stirring at 4° C. After the addition of cold 0.1M sodium bicarbonate, the pH was adjusted to 8.5 with 1N sodium hydroxide. To this solution was added 6 ml of 0.1M sodium bicarbonate containing 0.8 to 1.0 grams of derivatized cellulose and the mixture was rotated at 4° C. for 2 hours.

After the removal of excess DMS, the coupled, derivatized, cellulosic matrix was suspended in 9 ml of 0.1M sodium bicarbonate (4° C.) and 1.3 ml of goat antirabbit gamma globulin fraction (36 to 38 mg/ml) in 0.1M sodium bicarbonate (4° C.) and the mixture was rotated in a cold room. The immobilized, secondary antibody was then thoroughly washed with 0.1M sodium bicarbonate and finally suspended in barbital buffer, pH 8.0, containing 0.1% gelatin, to give a final volume of 25 ml.

Example 2 was repeated wherein the sole modification was the size of the microcrystalline cellulose used. The various other sizes of microcrystalline cellulose employed were microcrystalline cellulose Type 20 and microcrystalline cellulose Type 50 which had been hydrolyzed for 4 hours, 6 hours, 24 hours, and 64 hours.

EXAMPLE 3

Microcrystalline cellulose type 50 (1 gm) was added to a solution of 1.0 gm of cyanogen bromide (CNBr) in water at room temperature. The pH of the mixture was immediately adjusted to about 11.0 with 2N sodium hydroxide and maintained at this pH for 6 to 12 minutes by the controlled addition of 2N sodium hydroxide. After the pH stabilized at about 11, the mixture was allowed to stand an additional 5 to 10 minutes before the activated, cellulosic matrix was washed with 1.1 liters of 0.1N sodium bicarbonate at 4° C. to remove the excess CNBr.

The thoroughly washed, activated, cellulosic matrix was then suspended in 10 ml of 0.1N sodium bicarbonate and about 47 mgm of goat antirabbit gamma globulin in 1.3 ml of 0.1N sodium bicarbonate was added thereto. The suspension was then mixed at room temperature overnight.

The following day the immunochemical composite was washed with 600 ml of 0.1N sodium bicarbonate and 100 ml of barbital buffer (pH 8.0) containing 0.1% gelatin. Finally, the composite was suspended in the above gelatin containing barbital buffer to give a final solution of 25 ml.

Example 3 was repeated wherein the sole modification was the size of the microcrystalline cellulose used. The various other sizes of microcrystalline cellulose employed were microcrystalline cellulose Type 20 and microcrystalline cellulose Type 50 which had been hydrolyzed for 4, 6, 24, and 64 hours.

EXAMPLE 4

Second antibody solid preparations of microcrystalline cellulose Type 50 as prepared in Examples 2 and 3 were titered against $^{125}$I-thyroxine in the presence of about 1 μg of rabbit gamma globulin as follows:
20λ — barbital buffer pH 8.0 containing 3.5% BSA
100λ — $^{125}$I-thyroxine in barbital buffer pH 8.0 containing 2% BSA
100λ — rabbit antisera against thyroxine at a dilution of 1/1000 (containing about 1 μg rabbit IgG)
200λ — solid phase second antibody preparations In experiments in which the reactants were agitated, each tube was incubated at room temperature for one-half hour with shaking and subsequently centrifuged for 20 minutes at 1000 × g. The precipitates were suspended in 1.0 ml of barbital buffer, pH 8.0, containing 3.5% BSA and recentrifuged for 20 minutes at 1000 × g. However, in the experiments in which the reactants were not agitated, each tube was incubated at 37° C. for one-half hour and before centrifugation 1 ml of barbital buffer, pH 8, containing 3.5% BSA was added. Each tube was subsequently centrifuged at 1000 × g for 20 minutes.

In both of these experiments the labeled thyroxine is immunologically bound to its specific antibodies which are present as a fraction of approximately 1 microgram of rabbit gamma globulin. Thus, one is able to indirectly measure the units of second antibody bound to the different cellulose matrices by calculating the largest dilution of each of the solid phase precipitating antibody preparations to give maximal binding of labeled-thyroxine.

The units of activity were caluclated from the largest dilution, i.e., titer, of solid phase second antibody that resulted in maximal binding of the labeled antigen. The formula used to calculate the units of activity is as follows:

$$\frac{1}{\frac{\text{titer}}{\text{sample size}}} \times \begin{array}{l}\text{total volume of}\\ \text{solid phase anti-}\\ \text{body preparation}\end{array} = \begin{array}{l}\text{Units}\\ \text{of}\\ \text{Activity}\end{array}$$

wherein the sample size in our example is 200λ (0.2 ml) and wherein the total volume of solid phase secondary antibody preparation is 25 ml. Since these titers were done in the presence of 100λ of rabbit anti-thyroxine sera diluted 1/1,000, one actually looks for the largest dilution of solid phase second antibody capable of binding about 1 microgram of rabbit gamma globulin. The results of these calculations are listed in Tables I and II. As Tables I and II clearly depict, the titer of the goat antirabbit antisera coupled to the DMS derivatized finely divided cellulose was far superior to the corresponding CNBr coupled preparation of finely divided, microcrystalline cellulose. In fact, the titer of said DMS derivatized, finely divided cellulose which underwent no shaking was even superior to the shaken CNBr coupled preparations.

Table I

| Support | Protein Concentration of Antibody Containing Gamma Globulin Fraction | Titer Shaking | Units of Activity Recovered Shaking | Titer Nonshaking | Units of Activity Recovered Nonshaking | % Units Shaking / Units Nonshaking |
|---|---|---|---|---|---|---|
| 1 gram CNBr activated microcrystalline cellulose Type 50 | 47 mg of goat anti-rabbit gamma globulin | 1/1.6 | 212 | 0 | 0 | 0 |
| 1 gram CNBr activated microcrystalline cellulose Type 20 | " | 1/3.7 | 462 | 1/1.6 | 200 | 43.29% |
| 1 gram CNBr activated 4 hr. acid hydrolyzed microcrystalline cellulose Type 50 | " | 1/5 | 625 | 1/2.9 | 362 | 57.92% |
| 1 gram CNBr activated 6 hr. acid hydrolyzed microcrystalline cellulose Type 50 | " | 1/5 | 625 | 1/2.9 | 362 | 57.92% |
| 1 gram CNBr activated 24 hr. acid hydrolyzed microcrystalline cellulose Type 50 | " | 1/5 | 625 | 1/3.4 | 425 | 68.00% |
| 1 gram CNBr activated 64 hr. acid hydrolyzed microcrystalline cellulose Type 50 | " | 1/5.5 | 688 | 1/3.4 | 425 | 61.77% |

Table II

| Support | Protein Concentration of Antibody Containing Gamma Globulin Fraction | Titer Shaking | Units of Activity Recovered Shaking | Titer Nonshaking | Units of Activity Recovered Nonshaking | % Units Shaking / Units Nonshaking |
|---|---|---|---|---|---|---|
| 1 gram DMS activated microcrystalline cellulose Type 50 | 49 mg of goat anti-rabbit gamma globulin | 1/5 | 750 | 1/2 | 250 | 33.33% |
| 1 gram DMS activated microcrystalline cellulose Type 20 | " | 1/11.5 | 1438 | 1/5.1 | 638 | 44.37% |
| 1 gram DMS activated 4 hr. acid hydrolyzed microcrystalline cellulose Type 50 | " | 1/11.5 | 1438 | 1/7.0 | 875 | 60.85% |
| 1 gram DMS activated 6 hr. acid hydrolyzed microcrystalline cellulose Type 50 | " | 1/11.5 | 1438 | 1/7.0 | 875 | 60.85% |
| 1 gram DMS activated 24 hr. acid hydrolyzed microcrystalline cellulose Type 50 | " | 1/11.5 | 1438 | 1/7.0 | 875 | 60.85% |
| 1 gram DMS activated 64 hr. acid hydrolyzed microcrystalline cellulose Type 50 | " | 1/11.5 | 1438 | 1/7.0 | 875 | 60.85% |

Table III

| Support | Shaking $\frac{\text{Units of Activity by DMS}}{\text{Units of Activity by CNBr}}$ | Nonshaking $\frac{\text{Units of Activity by DMS}}{\text{Units of Activity by CNBr}}$ | $\frac{\text{Units of Activity by DMS Nonshaking}}{\text{Units of Activity by CNBr Shaking}}$ |
|---|---|---|---|
| Microcrystalline Cellulose Type 50 | $\frac{750}{212} = 3.54$ | $\frac{250}{0} =$ Indefinite | $\frac{250}{212} = 1.18$ |
| Microcrystalline Cellulose Type 20 | $\frac{1438}{462} = 3.11$ | $\frac{638}{200} = 3.19$ | $\frac{638}{462} = 1.38$ |
| 4 hr. acid hydrolyzed Microcrystalline Cellulose Type 50 | $\frac{1438}{625} = 2.30$ | $\frac{875}{362} = 2.42$ | $\frac{875}{625} = 1.40$ |
| 6 hr. acid hydrolyzed Microcrystalline Cellulose Type 50 | $\frac{1438}{625} = 2.30$ | $\frac{875}{362} = 2.06$ | $\frac{875}{625} = 1.40$ |
| 24 hr. acid hydrolyzed Microcrystalline Cellulose Type 50 | $\frac{1438}{625} = 2.30$ | $\frac{875}{425} = 2.06$ | $\frac{875}{625} = 1.40$ |
| 64 hr. acid hydrolyzed Microcrystalline Cellulose Type 50 | $\frac{1438}{688} = 2.09$ | $\frac{875}{425} = 2.06$ | $\frac{875}{625} = 1.27$ |

Table IV

| | Assay Time at 37° C. | Control Sera | | | | | | | | |
|---|---|---|---|---|---|---|---|---|---|---|
| | | Digoxin Beckman Control Serum | Thyroxine Beckman Control Serum | Triiodo-thyronine Beckman Control Serum | TSH Beckman Control Serum | TSH Beckman Control Serum Diluted ½ | Lederle I | Lederle II | Ortho I | Ortho II |
| Digoxin (ng/ml) | ½ hr. | 2.75 (2.0–2.7)* | — | — | — | — | 1.44 (.94–1.78) | >6.0 | .62 (.6–1.2) | 4.25 (3.2–5.2) |
| Triiodothyronine (ng/ml) | 2 hr. | — | 86 (90–110) | 222 (165–225) | 85 (70–90) | — | 116 (98–118) | 474 (409–457) | — | — |
| Thyroxine (μg/dl) | ½ hr. | — | 12.3 (12–20) | — | 5.0 (6–7) | — | 7.2 (6.4–9.6) | 16.1 (13.6–22) | — | — |
| Human Thyrotropin Stimulating Hormone (micro international units/ml) | 6 hr. | — | — | — | 77.0 (40–75) | 35.2 | 3.7 (3–4) | 2.6 (2.3–2.95) | 7.2 (3.9–7.9) | 32.2 (23–39) |

*Values in ( ) are those obtained with the conventional double antibody method.

Examples 4 was repeated except that the size of the microcrystalline cellulose used was varied. This variation, as above, entailed the use of microcrystalline cellulose Type 20 and microcrystalline cellulose Type 50 which had been hydrolyzed for 4, 6, 24, and 64 hours. The results of this data is also listed in Tables I and II.

An examination of Table I reveals several things. In the column entitled "Units of Activity Recovered Shaking", since the vial is being shook, all matrix sizes should be equally mixed and equally suspended and therefore the exposure of the CNBr covalently bound second antibody to the antigen is the same. However, it is readily apparent that the matrix size does influence the biological activity of the CNBr covalently coupled second antibody. This column indicates three basic groupings, namely, microcrystalline cellulose Type 50, microcrystalline cellulose Type 20, and microcrystalline cellulose Type 50 which has been hydrolyzed for 4 hours or more. The basic thrust of said column is that one cannot recover more activity by shaking a CNBr activated matrix than that recovered using a microcrystalline cellulose Type 50 which had been hydrolyzed for 4 hours.

In the column entitled "Units of Activity Recovered Nonshaking", suspendability of a particle, and therefore, matrix size, comes into play as well as the biological activity of the covalently coupled second antibody. Four subdivisions are found in this column, namely, microcrystalline cellulose Type 50, microcrystalline cellulose Type 20, microcrystalline cellulose Type 50 which has been hydrolyzed for 4 and 6 hours, and microcrystalline cellulose Type 50 which has been hydrolyzed for 24 and 64 hours, with maximum biological activity being found in the last group.

A similar comparison of Table II indicates the striking improvement of the novel immunochemical composites within the scope of this invention over the immunochemical composites of Table I. The column entitled "Units of Activity Recovered Shaking" has two basic subgroups instead of the three which appear in Table I. Namely, the microcrystalline cellulose Type 50 differs from microcrystalline cellulose Type 20 and smaller. This differential implies that one cannot obtain more biological activity than is recovered when using a microcrystalline cellulose Type 20. However, upon examining the column entitled "Units of Activity Recovered Nonshaking", one sees that the column is divided into three groups, namely microcrystalline cellulose Type 50, microcrystalline cellulose Type 20, and microcrystalline cellulose Type 50 which has been hydrolyzed for either 4, 6, 24, or 64 hours. One can conclude, therefore, that when one uses a microcrystalline cellulose or similar polysaccharide having a maximum dimension of 18 μ or less, the size of the matrix is not a limiting factor in determining the amount of activity recoverd. Further, one can see that although one does not obtain the degree of activity present when shaking, the nonshaking units of activity recovered using any of the novel immunochemical composites within the scope of this invention far exceed the amount of units of activity recovered shaking using an antibody directly coupled to a matrix via the CNBr process. The reason for this vast improvement is that this invention's composites effectively position the antibody at a distance removed from the matrix surface and thereby decrease the effect and influence of the matrix size on the biological reaction. Besides removing the antibody from the matrix surface, this invention also couples the antibody to a derivatized matrix via a coupling agent which, as noted above, does not in most instances adversely affect said antibody's immunological activity.

In addition to the above, the improved efficacy of this invention's novel immunological chemical composites enables one to use larger matrix sizes in a nonagitation procedure thereby making it possible for one to employ a centrifugation device with lower g's. The ability to use a centrifuge having a lower g rating is significant in that one working with this invention's novel immunological composites can now use conventional lab centrifuges and thereby avoid the high expense one would otherwise have to incur if he wished to practice a prior art method such as that of Chan et al.

As Table III dramatically depicts, one obtains about 27 to 40% increase using the novel immunochemical composites within the scope of this invention in a nonagitated procedure over the shaking procedure wherein the antibody is directly coupled to a matrix via the CNBr process.

Table IV compares the efficacy of employing the novel immunochemical composites within the scope of this invention with the conventional prior art double antibody method in various immunoassay tests. As Table IV indicates, the results obtained using the novel method and immunochemical composites within the scope of this invention compare favorably with respect to the prior art method using said conventional double antibody method. It should be noted that the RIA of thyroxine via the conventional double antibody method takes about 2 hours whereas an RIA employing the novel immunochemical composites within the scope of this invention takes but a half hour.

Based on this disclosure, many other modifications and ramifications will naturally suggest themselves to those skilled in the art of immunoassay procedures. These are intended to be comprehended as within the scope of this invention.

The embodiments of the invention in which an exclusive property or privilege is claimed are defined as follows:

1. A method of separating free from bound fractions in an immunoassay procedure of the type wherein a solution is contacted with a composite comprising a finely divided, activated, polysaccharide matrix covalently coupled to a primary antibody, wherein the improvement comprises contacting said solution with a composite comprising a finely divided, derivatized, polysaccharide matrix covalently coupled to an antibody selected from a group consisting of primary and secondary antibodies via a bifunctional coupling agent having a formula

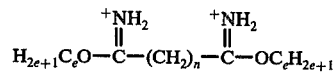

wherein $n$ is an integer from 1 to 6 and wherein $e$ is an integer from 1 to 2; and wherein said finely divided, derivatized, polysaccharide matrix comprises a finely divided, activated, polysaccharide matrix having an average wet maximum dimension of 1 to 18 microns, coupled to an $\alpha,\omega$-diaminospacer via one of said $\alpha,\omega$-diamonospacer's amino groups.

2. The method of claim 1 wherein said immunochemical composite has a formula

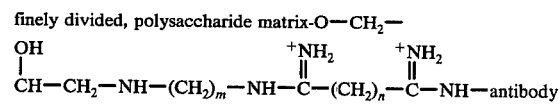

wherein $m$ is an integer from 1 to 12.

3. The method of claim 2 wherein said polysaccharide matrix is selected from a group consisting of cellulosic polymers, dextran polymers, agarose, and derivatives thereof, wherein $m$ is an integer from 4 to 6, and wherein $n$ is an integer from 4 to 6.

4. The method of claim 3 wherein said polysaccharide matrix is selected from the group consisting of cellulosic polymers and derivatives thereof having a wet length of 10 to 15 $\mu$.

5. The method of claim 4 wherein said antibody is a secondary antibody.

6. The method of claim 5 wherein a tube containing said composite remains essentially motionless during an incubation step.

7. The method of claim 6 wherein said immunoassay procedure is a radioimmunoassay procedure.

8. The method of claim 1 wherein said immunoassay procedure is a radioimmunoassay procedure.

9. An immunochemical composite, for separating free from bound fractions in an immunoassay procedure, comprising a finely divided, derivatized, polysaccharide matrix covalently coupled to an antibody selected from a group consisting of primary and secondary antibodies via a bifunctional coupling agent having a formula

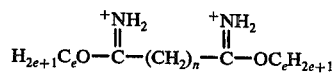

wherein $n$ is an integer from 1 to 6 and wherein $e$ is an integer from 1 to 2; and wherein said finely divided, derivatized, polysaccharide matrix comprises a finely divided, activated polysaccharide matrix having an average wet maximum dimension of 1 to 18 microns, coupled to an $\alpha,\omega$-diaminospacer via one of said $\alpha,\omega$-diaminospacer's amino groups.

10. The immunochemical composite of claim 9 having a formula finely divided, polysaccharide matrix-O—CH$_2$—

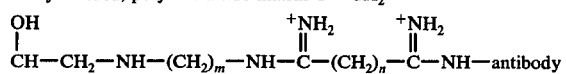

wherein $m$ is an integer from 1 to 12.

11. The immunochemical composite of claim 10 wherein said polysaccharide matrix is selected from a group consisting of cellulosic polymers, dextran polymers, agarose, and derivatives thereof, wherein $m$ is an integer from 4 to 6 and wherein $n$ is an integer from 4 to 6.

12. The immunochemical composite of claim 11 wherein said polysaccharide matrix is selected from the group consisting of cellulosic polymers and derivatives thereof having a wet length of 10 to 15 $\mu$.

13. The immunochemical composite of claim 12 wherein said antibody is a secondary antibody.

* * * * *